United States Patent [19]
Dirix et al.

[11] Patent Number: 5,389,379
[45] Date of Patent: Feb. 14, 1995

[54] PROCESS FOR THE PREPARATION OF BIOLOGICALLY ACTIVE MATERIAL CONTAINING POLYMERIC MICROCAPSULES

[75] Inventors: Cardina A. M. C. Dirix; Hendrikus J. M. Kamp, both of Westervoort; Anthonius P. Sam, Heesch, all of Netherlands

[73] Assignee: Akzo N.V., Arnhem, Netherlands

[21] Appl. No.: 17,925

[22] Filed: Feb. 16, 1993

[30] Foreign Application Priority Data

Feb. 18, 1992 [EP] European Pat. Off. ........... 92200466

[51] Int. Cl.$^6$ ........................ A61K 9/48; A61K 9/14; B01J 13/04; B01J 13/20
[52] U.S. Cl. .................................. 424/451; 424/489; 264/4.1; 264/4.6
[58] Field of Search ................. 424/451, 489; 264/4.1, 264/4.6

[56] References Cited

U.S. PATENT DOCUMENTS

| | | | |
|---|---|---|---|
| 4,389,330 | 6/1983 | Tice et al. | 252/316 |
| 4,897,267 | 1/1990 | Bontemps et al. | 424/423 |
| 5,091,187 | 2/1993 | Haynes | 424/450 |

FOREIGN PATENT DOCUMENTS 2491351 4/1982 France .
9013780 11/1990 WIPO .

OTHER PUBLICATIONS

Sefton et al., Journal of Pharaceutical Sciences, "Ethylene-Vinyl Acetate Copolymer Microspheres for Controlled Release of Macromolecules", vol. 73, No. 12, Dec., 1984.

*C.E.*, vol. 97 (Nov., 1990).

*Primary Examiner*—G. S. Kishore
*Assistant Examiner*—Carlos Azpuru
*Attorney, Agent, or Firm*—William M. Blackstone; Mary E. Gormley

[57] ABSTRACT

A process for the preparation of microcapsules containing biologically active material is disclosed. The process involves dissolving a polymer into a solvent into which the active material is also introduced; atomizing the resulting suspension or solution and collecting the droplets in a non-solvent for the polymeric droplets containing active material, resulting in coagulation. Subsequently, the coagulated droplets are hardened in a second non-solvent.

7 Claims, 2 Drawing Sheets

PROCESS FOR THE PREPARATION OF BIOLOGICALLY ACTIVE MATERIAL CONTAINING POLYMERIC MICROCAPSULES

FIELD

The invention relates to a process for the preparation of biologically active agent containing polymeric microcapsules, which process involves dissolving a polymer into a solvent into which the active material is also introduced and forming droplets therefrom from which the solvent is subsequently removed.

STATE OF THE ART

A similar process is described in EP 301 969A1 (corresponding to U.S. Pat. No. 4,897,267) with the droplets being formed by emulsification of the active material containing polymer solution in a medium, usually mineral oil, which is not miscible with the solvent. The droplets are freed from the solvent by evaporation, after which a suspension of polymeric particles is obtained. Emulsification is also the principle of the process described in FR-A-2 491 351. In this process microcapsules are prepared by emulsifying active material and a polymer—both dissolved or dispersed in a solvent, for example dichloromethane—in an aqueous solution, after which the solvent is partly evaporated and further washed out through filtration, extraction and washing with water. Hardening occurs slowly during the process of evaporation and extraction. A disadvantage of this method is that it can only be applied batch-wise and that clotting of the filter can seriously hamper the process. A drawback to emulsification methods in general is the limited choice one has for the polymer solvent, a sufficiently soluble non-aqueous medium which must be volatile. Another drawback is that, upon emulsification of the polymer solution, the active material it contains may end up in the dispersion medium rather than in the polymer solution droplets. Further, such processes are not easily up-scaled.

Another process for making microspheres from Nukem GmbH of Alzenau, Germany is somewhat described in C.E. vol. 97 (November 1990). The spheres are produced by means of an injection moulding process from an initial liquid phase which is a fusion, suspension or solution. The liquid phase is passed through nozzles of a chosen diameter. The nozzle head is oscillated at intervals to interrupt the liquid phase flow resulting in homogeneously sized drops. The drops fall through a "reaction zone" where an undescribed coagulation process is initiated. Thereafter the microspheres are further shaped by an undescribed chemical reaction with a gas or liquid phase. The entire process is complicated and not very well described.

A different process for making microcapsules is atomizing a polymer solution into which solution the active material is also introduced, and subsequently removing the solvent from the droplets. Such a method is described in WO-A-9 013 780. In this method, the polymer/active agent mixture is atomized into a vessel containing a liquid non-solvent, alone or frozen and overlayered with a liquified gas, at a temperature below the freezing point of the polymer/active agent solution. The cold liquified gas or liquid immediately freezes the polymer droplets. As the droplets and the non-solvent for the polymer are warmed, the solvent in the droplets thaws and is extracted into the non-solvent, resulting in hardened microspheres. Drawbacks of this hardening method are the low temperature and long reaction time necessary for obtaining uniform spherical non-aggregated polymeric microsheres. Therefore, this method is unattractive for large scale production.

It would be an improvement in the art to have a relatively simple and straight-forward process for making microcapsules.

SUMMARY OF THE INVENTION

The invention provides a process for the preparation of polymeric microcapsules containing a biologically active agent which process is efficiently upscalable. The polymer solution droplets are formed by atomization in such a manner that the droplets contain the active material. These droplets are collected and coagulated in a non-solvent. The invention includes a process of the aforementioned type characterized in that the coagulated droplets are subsequently transferred into a second non-solvent.

DETAILED DESCRIPTION OF PREFERRED EMBODIMENTS

Figure 1:
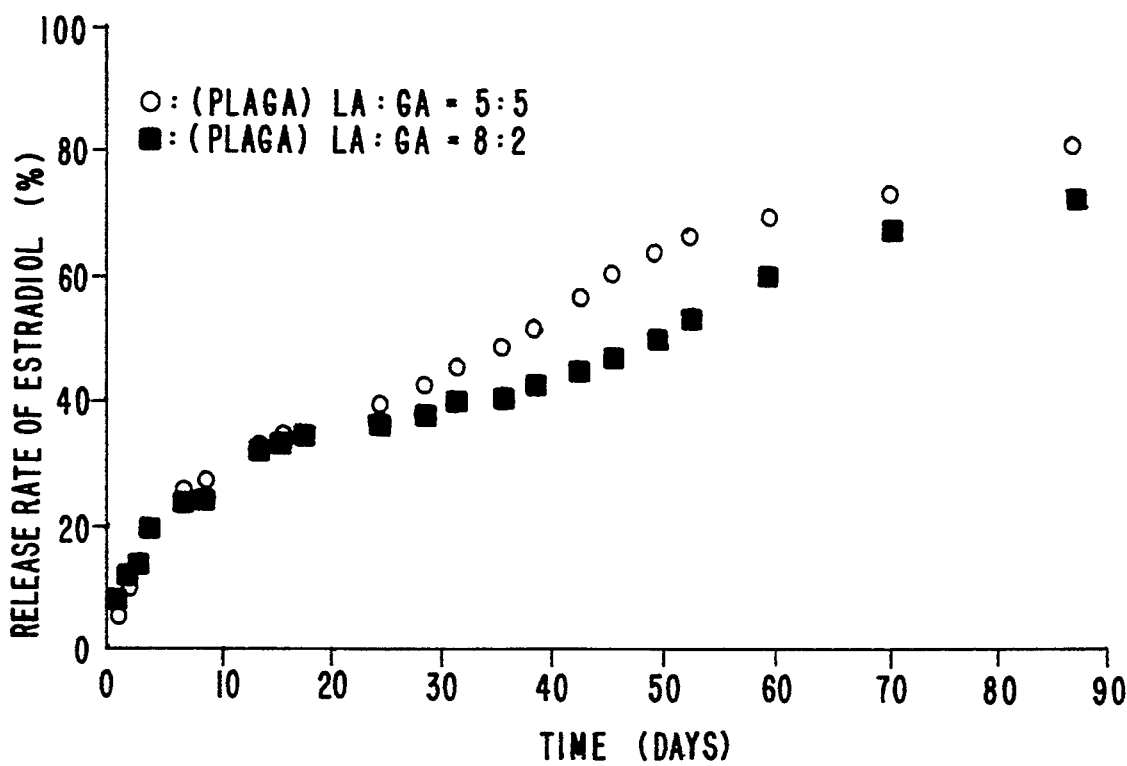
FIG. 1 depicts the release of estradiol from microcapsule prepared according to the invention.

Of course, the extent to which a liquid medium functions as a solvent or a non-solvent is dependent on the polymer type and biologically active material chosen. The artisan generally knows which solvent to use with which polymer and which non-solvent. Employing such knowledge, the process is essentially a fast and simple method for preparing polymeric microcapsules, especially microcapsules for in vivo use. The solvent and/or non-solvent may consist of a mixture of solvents and non-solvents.

Preferentially, both the polymer and the biologically active agent will be soluble in the chosen solvent at the temperature used during the atomization process. Also, preferentially, neither the polymer nor the biologically active material will be soluble in the selected non-solvent at the relevant process temperature. The solvent may also contain some non-solvent, so long as the concentration of such non-solvent is sufficiently low so as not to affect detrimentally the solubility of the biologically active agent or agents in the solvent.

Solubilities of various biologically active materials are given in, for example, Gennaro et al., *Remington's Pharmaceutical Sciences*, (Mack Publishing Co. 18$^{th}$ ed. 1990), and *The Merck Index*, (11$^{th}$ ed. 1989). Solubilities of various polymers are also available in various well-known texts.

Especially with regard to controlled release behaviour, parameters like particle size and particle size distribution are of importance. In preparing biologically active agent-containing microcapsules, the required values for these parameters, and therefore also the process conditions are determined by release-studies. A general rule, applicable to all polymers and all biologically active substances cannot be given.

In a previously described process (i.e. that disclosed in EP 301,969 and in FR-A-2 491 351) the parameters are determined by the emulsifying step, e.g. by the manner in which stirring is carried out. As is commonly known in the art, such a step should be adapted upon upscaling, of which the impact on surface and the impact on volume are different. In this respect, such a process is disadvantageous, since upscaling will lead to different results than those attained on a small scale, and new release studies will be needed.

In view of the above mentioned drawbacks, atomization methods are advantageous. After the process conditions have been determined, process upscaling can be effected simply by increasing the number of atomizing nozzles and by using a larger collecting capacity. In this way, the crucial step of forming the droplets in the atomization process is not affected by upscaling.

"Atomizing" may be accomplished by commercially available atomizers. Commercially available atomizers are also used to humidify air or goods, to inject gas into liquids, and to degas liquids. By using the term "atomizing", within the field of spraying liquids, it is clear that droplets are formed having a size of about 10–1000 $\mu$m, which size also indicates that the particles formed should be called "microcapsules". Of course, the droplet's size, which directly determines the particle size, can be tuned by adjusting the atomizer.

In this respect it is preferred to use an ultrasonic atomizer, which permits easy adjustment of particle size by varying the oscillation frequency. Ultrasonic atomizers are marketed, for example, by Lechler and are described in the technical information bulletin which accompanies the atomizer.

In the instant process, the droplets formed by ultrasonic atomization are first collected in a non-solvent. In this first step, the droplets remain intact, coagulate and some polymer solvent is extracted into the non-solvent. Subsequently, the first non-solvent is exchanged by a second non-solvent for hardening the microspheres.

The process according to the present invention may be applied to all polymers, provided that a suitable solvent and suitable non-solvent exist. A solvent can be regarded as suitable if the viscosity of the polymer solution can be kept low enough for the solution to be atomized. A non-solvent can be used in the collection step if the droplets remain intact, which means that polymeric films floating on the non-solvent are not formed and deformation or aggregation of the coagulated droplets is not observed. A non-solvent for the hardening step can be used if both the polymer solvent and the non-solvent of the collecting- and coagulating step are extracted by it and if the polymer hardens in this solvent. Conditions leading to favourable results should be determined per polymer type.

Polymers and co-polymers which are used as carrier medium for injectable controlled release dosage forms for therapeutics generally are biologically degradable. Preferably the polymer or co-polymer will contain bonds which can be hydrolysed to form non-toxic degradation products. Examples of such polymers include poly(glycolic acid), poly(lactic acid), copolymers of glycolic acid and L-lactic acid, gelatin, agar, starch, arabinogalactan, albumin, collagen, natural or synthetic materials or polymers, such as poly($\epsilon$-caprolactone), poly($\epsilon$-caprolactone-lactic acid ketone), poly($\epsilon$-caprolactone-glycolic acid ketone), poly($\beta$-hydroxybutyric acid), polyethylene oxide, polyethylene, poly(alkyl-2-cyanoacrylate), hydrogels such as poly(hydroxyethyl methacrylate) or block copolyether-esters, polyamides, e.g., poly(acrylamides), poly(amino acids)- (i.e. L-leucine, L-aspartic acid, $\beta$-methyl-L-aspartate, $\beta$-benzyl-L-aspartate, glutamic acid and the like), poly(2-hydroxy-ethyl-DL-aspartamide), poly(ester urea), poly(L-phenyl-alanine/ethyleneglycol/1,6-diisocyanato-hexane), poly(methylmethacrylate), polyphosphazenes, polymers and copolymers of poly(hydroxybutyrate) and poly(hydroxyvalerate), poly(orthoesters), poly(orthocarbonates), poly(anhydrides), poly(alkyl-$\alpha$-cyanoacrylates), poly(urethanes), poly(depsipeptides) and aliphatic polyesters.

Polymers of glycolic acid, lactic acid and copolymers of glycolic and lactic acid (PLAGA) are preferred. In the present field this preference is common, due to the good biocompatibility and release behaviour of these polymers. A further advantage to these polymers is their solubility in acetone, which to a certain extent is biocompatible. A preferred solvent for use with PLAGA is acetone, preferred first non-solvents for use with PLAGA are ethanol, water, and mixtures thereof. A preferred second non-solvent is water.

A further advantage of the invention is that it can be carried out at ambient temperature.

In the above-cited EP 0 301 969, the polylactide used is also dissolved in acetone, but due to the required evaporation of the solvent a heavier oil is needed to collect the polymer solution droplets, which eventually will lead to the polymeric microcapsules being contaminated. In using the commonly preferred polymers of lactic and glycolic acid a preferred embodiment of the process according to the invention has the further advantage that the polymeric microcapsules may be obtained in water, which is a strong non-solvent for those polymers and will not leave any contamination on the microcapsules. By virtue of the following general procedure, in fact all polymers for which water acts as a strong non-solvent can eventually be collected in water.

The general procedure according to the preferred embodiment of the present invention comprises using a medium which acts as a suitable non-solvent for the polymer to collect the atomized droplets and, after a residence time of several minutes to a few hours, transferring the particles to water. Directly collecting the atomized droplets of PLAGA in water generally will lead to a thin polymeric film on the water surface instead of microcapsules being formed. Specifically applied to the above preferred polymers, the atomized polymer solution droplets are first collected in ethanol. Hardening of the microcapsules in ethanol at ambient pressure and temperature is not possible; it inevitably leads to aggregation of the microparticles and/or gelation of PLAGA on the long term. Surface active agents may be added to the non-solvent during extraction of the (polymer) solvent to reduce the possibility of aggregation of the microcapsules.

In the presently most preferred embodiment, the microcapsules, as collected in the non-solvent, are vibrated loose by means of ultrasonic vibration.

As used herein, "a biologically active agent" is a substance having pharmacological or physiological effect. Microcapsules containing such substances in particular find use in the controlled release of drugs.

Preferred biologically active materials are medicinal compounds, especially those intended for chronic administration. Such medicinal compounds include peptides, such as LHRH antagonists; steroids; proteins, such as growth hormone or insulin; cytostatics, oligosaccharides and polysaccharides.

For veterinary medicine they can be used to deliver a very wide range of active ingredients e.g. glucocorticoids, gestagens, adrenergic agents, β-blockers, sedatives, and vaccines (adjuvants).

They may also be used to deliver insecticides, herbicides, pheromones and "repellants" to a local environment.

The invention is further explained by reference to the following EXAMPLES.

EXAMPLE I

Procedure for manufacturing 10 g of estradiol loaded (5%) PLAGA microcapsules by the method according to the invention:

a. Dissolve 500 mg of estradiol in 10 g of acetone.
b. Dissolve 9.5 g of PLAGA in 30 ml of acetone.
c. Add the estradiol solution to the PLAGA solution and homogenize.
d. Atomize the estradiol/PLAGA solution with the Ultrasonic Atomizer US1 (Lechler).
e. Use 500 ml of ethanol as initial collection and coagulation medium.
f. Exchange after ½ hour the ethanol for the same volume of purified water.
g. Collect the hardened microcapsules after 1 hour by filtration.
h. Wash the microcapsules with purified water.
i. Dry the microcapsules at room temperature for 16 hours in vacuo.
j. Screen the microcapsule preparation through a 150 μm sieve.

EXAMPLE II

Peptide and protein loaded PLAGA microcapsules are prepared in the same way, except for the fact that the active agents are not dissolved, but suspended in the PLAGA acetone solution.

EXAMPLE III-VI

Figure 2:
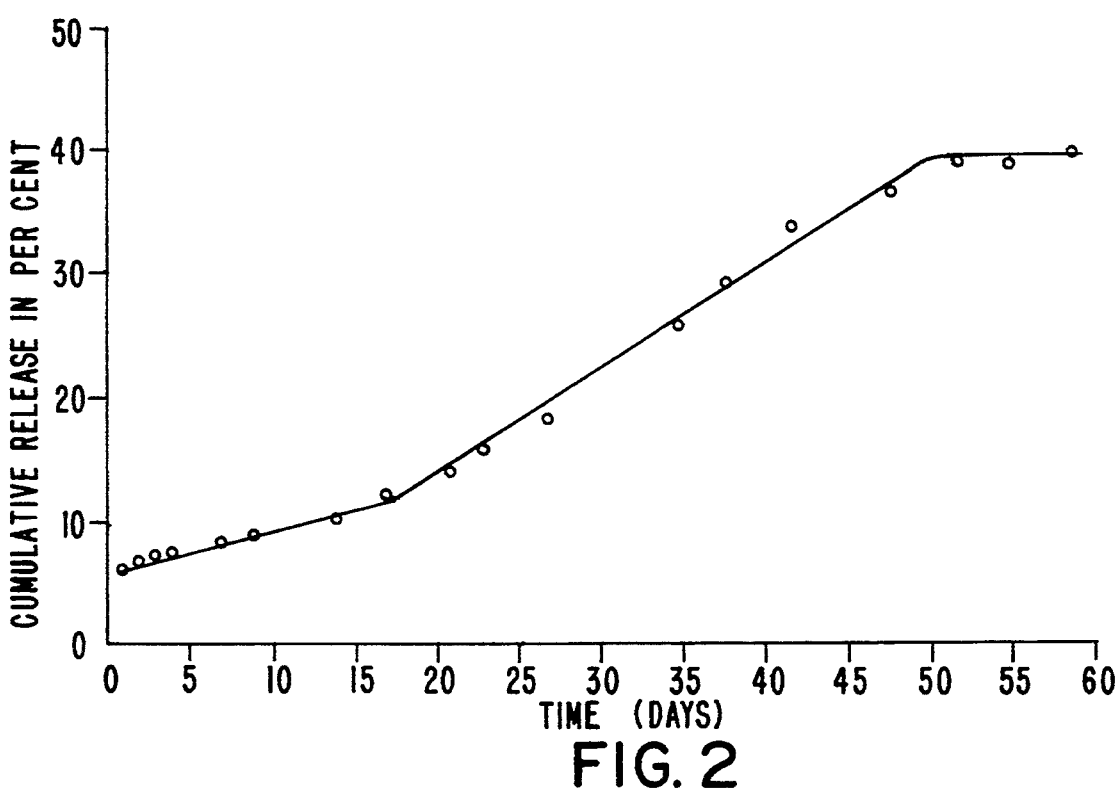
FIG. 2 depicts the release of the hexapeptide H-Gly-Gly-Phe-Met($O_2$)-D-Lys-Phe-OH (a $\beta$-endorphin 62–67 derivative) from microcapsule prepared according to the invention.
Figure 3:
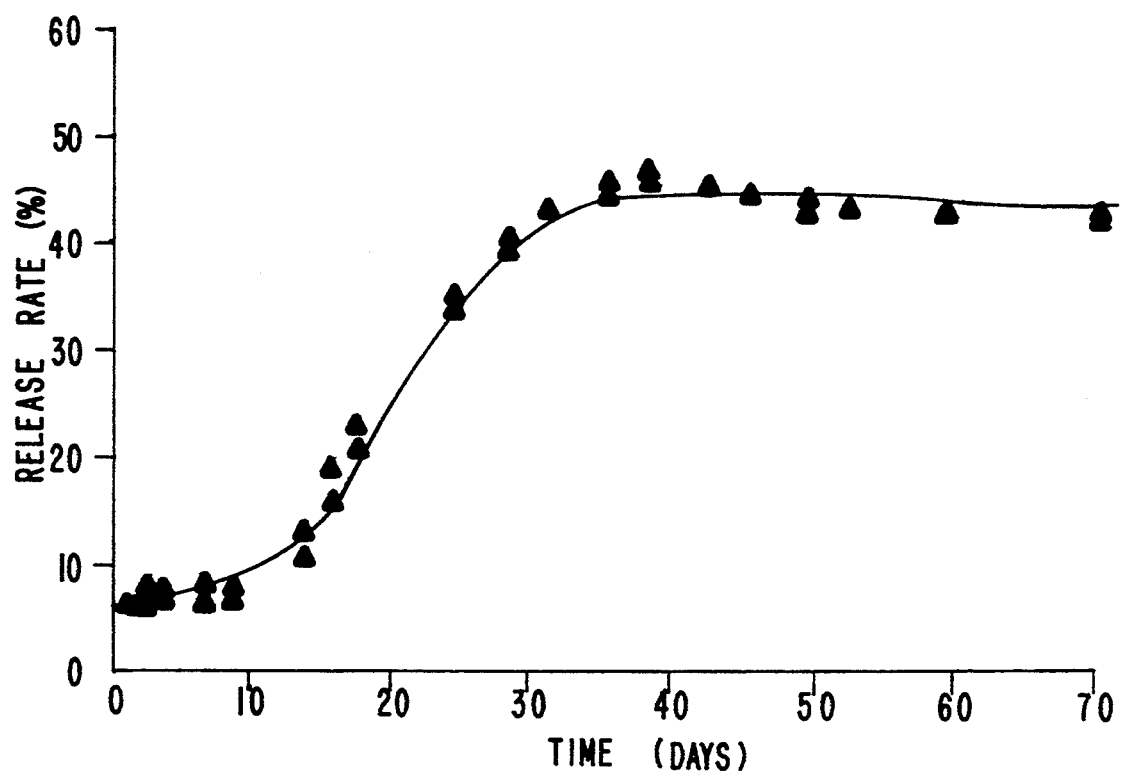
FIG. 3 depicts the release of the hexapeptide Org 2766 (H-Met$(O)_2$-Glu-His-Phe-D-Lys-Phe-OH) from microcapsules prepared according to the invention.
Figure 4:
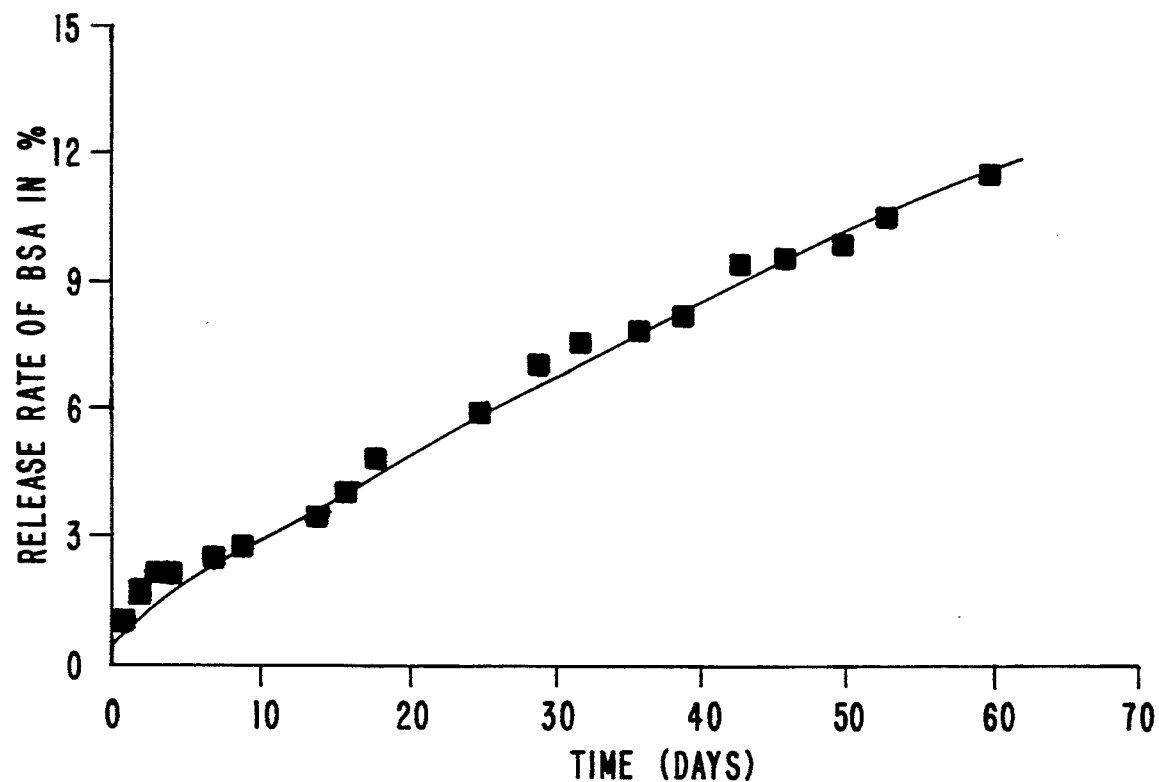
FIG. 4 depicts the release rate of bovine serum albumin from microcapsules prepared according to the invention.

Release studies on microcapsules made according to the invention were carried out on microcapsules containing a steroid (FIG. 1); different oligopeptides (FIGS. 2 and 3); and a protein (FIG. 4).

References herein to specific examples or embodiments should not be constructed as limitations to the scope of the invention which is defined by the appended claims.

We claim:

1. A process for the preparation of polymeric microcapsules comprising a biologically active agent, said process comprising mixing an active agent with a solvent to form a solution or suspension, dissolving a polymer in a solvent, which may be the same solvent used for dissolving or suspending the active agent, atomizing the formed solution or suspension, subsequently collecting the thus formed droplets in a non-solvent, and transferring the coagulated droplets into a second non-solvent.

2. The process according to claim 1, wherein the atomization process is ultrasonic atomization.

3. The process according to claim 1, wherein the polymer is biodegradable.

4. The process according to claim 1, wherein the polymer is a copolymer of lactic acid and glycolic acid.

5. The process according to any claim 1, wherein the second non-solvent is water.

6. The process according to claim 1, wherein the polymer is dissolved in acetone, the first non-solvent is ethanol or an ethanol-water mixture, and the second non-solvent is water.

7. The process according to claim 1, wherein the solution or suspension to be atomized comprises a non-solvent in an amount sufficiently small that it does not affect the solubility of the active agent.

* * * * *